United States Patent [19]

Rivetti et al.

[11] Patent Number: 4,469,897
[45] Date of Patent: Sep. 4, 1984

[54] PROCESS FOR PREPARING MONOALKYLETHERS OF HYDROQUINONE AND ITS DERIVATIVES

[75] Inventors: Franco Rivetti, Schio; Ugo Romano, Vimercate; Nicola Di Muzio, Peschiera Borromeo, all of Italy

[73] Assignee: Anic S.p.A., Palermo, Italy

[21] Appl. No.: 313,677

[22] Filed: Oct. 21, 1981

[30] Foreign Application Priority Data

Nov. 13, 1980 [IT] Italy ............................... 25933 A/80
Nov. 13, 1980 [IT] Italy ............................... 25934 A/80

[51] Int. Cl.³ ............................................ C07C 41/09
[52] U.S. Cl. ................................................... 568/650
[58] Field of Search ......................................... 568/650

[56] References Cited

U.S. PATENT DOCUMENTS 2,615,051 10/1952 Grote .................................. 568/650
2,781,404 2/1957 Rosenwald .......................... 568/650

Primary Examiner—Bernard Helfin
Attorney, Agent, or Firm—Hedman, Gibson, Costigan & Hoare

[57] ABSTRACT

A method for preparing monoalkylethers of hydroquinone and of substituted hydroquinones of general formula

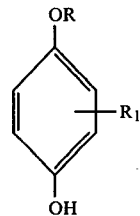

in which R is an alkyl group and $R_1$ is hydrogen or an alkyl group, wherein a hydroquinone compound of general formula

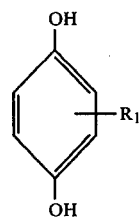

is reacted with an alcohol or formula R-OH in the presence of transition metal salts, either in the presence or in the absence of air or oxygen.

10 Claims, No Drawings

PROCESS FOR PREPARING MONOALKYLETHERS OF HYDROQUINONE AND ITS DERIVATIVES

This invention relates to a process for preparing monoalkylethers of hydroquinone and of substituted hydroquinones, of general formula

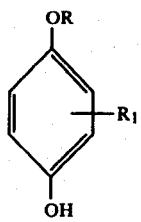

in which R is alkyl, and $R_1$ is H or alkyl.

It is known to synthesise hydroquinone ethers using aliphatic alkylsulphates or halides in the presence of bases.

Besides using relatively costly and often highly toxic alkylating agents such as dimethyl sulphate, the drawbacks of these methods include the problem of eliminating by-products such as $Na_2SO_4$ and NaCl, and the formation of mixtures of the corresponding monoethers, which generally constitute the required products, and diethers.

It is also known that hydroquinones can be etherified by alcohols in the presence of strong acids in the liquid phase or by acid catalysts in the vapour phase.

These reactions generally have rather low yields, and require high temperatures which favour the formation of tarry residues and prevent good selectivity of the required products being attained.

The etherification of hydroquinones by methanol/methyl acetate mixtures in the presence of triethylamine at 200°–250° C. has been described recently (U.S. Pat. No. 3,911,022). However, the reaction leads to the formation of mixtures of monoethers and diethers.

Finally, the selective preparation of hydroquinone monoethers has been claimed (British Pat. No. 1,557,237) by reacting mixtures of hydroquinones and the corresponding quinones with methanol in the presence of dehydrating acids. Hydroquinone monoalkyl ethers are widely used in the chemical industry. For example, hydroquinone monomethyl ether (p-methoxyphenol) is used in manufacturing antioxidants, pharmaceutical products, plasticisers and dyestuffs, as a stabiliser for chlorinated hydrocarbons and ethylcellulose, as an inhibitor for acrylic monomers etc.

Tert-butyl-hydroquinone monomethyl ether (3-tert-butyl-4-hydroxy anisole) is widely used as an antioxidant, especially in the foodstuffs field (BHA).

According to the present invention, a hydroquinone compound of general formula

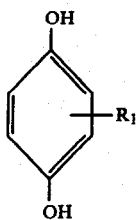

$R_1$ = H, alkyl is reacted with an alcohol of formula R—OH (R=alkyl) in the presence of transition metal salts, preferably iron or copper salts, either in the presence or in the absence of oxygen or air. When operating in the absence of oxygen, bivalent copper or trivalent iron salts are used.

The alcohol is preferably used both as the alkylating medium and as the solvent for the reaction system, but the reaction can also comprise the use of a suitable solvent. The hydroquinone substrate concentration in the reaction system is not critical and is limited in practice only by solubility, but there must be a molar excess of alcohol present.

If the reaction is carried out in the absence of air or oxygen, the inorganic salt is used in a weight ratio which varies preferably between 1:50 and 1:1 with respect to the hydroquinone substrate.

Examples of inorganic salts which can be used for the purposes of the reaction are chlorides and sulphates of bivalent copper and trivalent iron. The reaction is preferably carried out at a temperature of between 25° and 150° C. On termination, the product can be separated by distillation under reduced pressure or by solvent extraction. The reaction has consistent advantages over the known art in that it selectively produces the monoether of the hydroquinone substrate (diether formation is not observed) at high yields, using particularly mild conditions and without requiring costly or toxic reagents, and in addition does not give rise to the formation of by-products which are difficult to eliminate.

If the reaction is carried out in the presence of air or oxygen, the inorganic salt is used in a weight ratio which varies preferably between 1:1000 and 1:2 with respect to the hydroquinone substrate. Examples of inorganic salts which can be used for the reaction are chlorides and sulphates of copper in valency states 1 and 2 and of iron in valency states 2 and 3.

Said salts can be used either as such or supported on suitable materials, for example by means of ion exchange on sulphonated styrene resins. This facilitates separation of the inorganic material from the mixture at the end of the reaction and its recovery for reuse in a successive reaction.

The oxygen or air can be fed to the reaction system by forming a blanket at atmospheric or above-atmospheric pressure, or by bubbling it into the liquid phase. The reaction is carried out preferably at a temperature between 25° and 150° C. On termination, the product can be separated either by distillation under reduced pressure or by solvent extraction.

Some non-limiting examples of the process according to the invention are given hereinafter for its better understanding.

EXAMPLE 1

5.0 g of hydroquinone, 40 cm³ of methanol and 0.5 g of cupric chloride are fed into a teflon-lined autoclave having an internal capacity of 100 cm³. The autoclave is purged with nitrogen and is kept for 4 hours at 105° C. On termination of the reaction, an analysis of the mixture indicates the formation of 2.6 g of hydroquinone monomethyl ether (conversion 55%, selectivity 87%).

EXAMPLE 2

The reaction described under example 1 is repeated using 1.0 g of cupric chloride and keeping the autoclave at 105° C. for 2.5 hours. 4.1 g of hydroquinone monomethyl ether are obtained (conversion 85%, selectivity 87%).

EXAMPLE 3

5.0 g of hydroquinone, 40 cm$^3$ of methanol and 1.0 g of anhydrous iron trichloride are fed into the autoclave. The autoclave is purged with nitrogen and kept at 105° C. for 4 hours.

On termination of the reaction, 2.9 g of hydroquinone monomethyl ether are obtained (conversion 55%, selectivity 96%).

EXAMPLE 4

5.0 g of hydroquinone, 40 cm$^3$ of methanol and 0.5 g of ferric sulphate are fed into the autoclave.

The autoclave is purged with nitrogen and kept at 105° C. for 3 hours.

1.3 g of hydroquinone monomethyl ether are obtained (conversion 25%, selectivity 97%).

EXAMPLE 4A (comparative)

5.0 g of hydroquinone and 40 cm$^3$ of methanol are fed into the autoclave. It is pressurised to 5 kg/cm$^2$ with O$_2$ and kept at 125° C. for 3 hours. On termination of the reaction, gas chromatography analysis indicates the absence of formation of hydroquinone monomethyl ether.

EXAMPLE 5

5.0 g of tert-butyl-hydroquinone, 40 cm$^3$ of methanol and 1.0 g of cupric chloride are fed into the autoclave. The autoclave is purged with nitrogen and kept at 105° C. for 2.5 hours. On termination of the reaction, mixture analysis indicates the formation of 4.4 g of tert-butylhydroquinone monomethyl ether (BHA) (conversion 100%, selectivity 82%). The two BHA isomers (3-tert-butyl-4-hydroxyanisole and 2-tert-butyl-4-hydroxyanisole) are formed in a weight ratio of 99:1.

EXAMPLE 5A (comparative)

4.0 g of hydroquinone, 1.0 g of p-quinone and 40 cm$^3$ of methanol are fed into the autoclave.

After 2 hours at 125° C., gas chromatography analysis of the reaction mixture indicates the formation of 0.20 g (3%) of hydroquinone monomethyl ether.

EXAMPLE 6

5.0 g of hydroquinone, 0.20 g of FeSO$_4$.7H$_2$O and 40 cm$^3$ of methanol are fed into an autoclave of 100 cm$^3$ of internal capacity, internally lined with teflon.

The autoclave is pressurised to a pressure of 5 kg/cm$^2$ with O$_2$ and heated to 125° C. for 3 hours. Gas chromatography analysis of the mixture on termination of the reaction indicates the formation of 3.8 g of hydroquinone monomethylether (conversion 95%, selectivity 71%).

EXAMPLE 7

The reaction described under example 1 is repeated using 0.04 g of FeSO$_4$.7H$_2$O and pressurising the autoclave to 2 kg/cm$^2$ with O$_2$.

2.4 g of hydroquinone monomethyl ether are formed after 3 hours at 125° (conversion 60%, selectivity 71%).

EXAMPLE 8

5.0 g of hydroquinone, 0.04 g of CuCl and 40 cm$^3$ of methanol are fed into the autoclave. The autoclave is pressurised to 5 kg/cm$^2$ with O$_2$, and is kept at 125° for 2 hours.

On termination of the reaction, gas chromatography analysis of the mixture indicates the formation of 3.1 g of hydroquinone monomethyl ether (conversion 90%, selectivity 61%).

EXAMPLE 9

5.0 g of tert-butyl-hydroquinone, 0.20 g of FeSO$_4$.7H$_2$O and 40 cm$^3$ of methanol are fed into the autoclave.

It is pressurised to 5 kg/cm$^2$ with O$_2$ and kept at 125° C. for 3 hours. 2.6 g of tert-butyl-hydroquinone monomethyl ether (BHA) are obtained (conversion 80%, selectivity 60%). The two BHA isomers (3-tert-butyl-4-hydroxyanisole and 2-tert-butyl-4-hydroxyanisole) are formed in a weight ratio of 98:2.

EXAMPLE 10

250 g of hydroquinone, 5.0 g of FeSO$_4$.7H$_2$O and 2 liters of methanol are fed into a 3 liter autoclave lined internally with ceramic material.

The autoclave is heated to 125° C., and an air stream of 35 Nl/hr is fed in through a dip tube while keeping the total pressure of the system at 20 kg/cm$^2$, and maintaining the system under stirring. After 3 hours, the autoclave is cooled and the contents discharged. By means of distillation under reduced pressure, 150 g (53%) of hydroquinone monomethyl ether are obtained.

EXAMPLE 11

5.0 g of hydroquinone, 0.25 g of CuCl$_2$ and 40 cm$^3$ of methanol are fed into the autoclave.

The autoclave is pressurised to 3 kg/cm$^2$ with O$_2$ and kept at 85° C. for 1.5 hours.

Gas chromatography analysis of the reaction mixture indicates the formation of 3.9 g of hydroquinone monomethyl ether (conversion 95%, selectivity 73%).

EXAMPLE 12

The reaction described in example 8 is repeated with the autoclave pressurised to 3 kg/cm$^2$ with air. After 5 hours at 85° C., 4.0 g of hydroquinone monomethyl ether form (conversion 80%, selectivity 89%).

The autoclave is cooled, the gas is bled off and the autoclave is again blanketed with air at 3 kg/cm$^3$. After a further 1.5 hours at 85° C., 4.4 g of hydroquinone monomethyl ether are found in the reaction mixture (conversion 95%, selectivity 82%).

EXAMPLE 13

5.0 g of hydroquinone, 0.5 g of CuCl$_2$ and 40 cm$^3$ of methanol are fed into the autoclave.

The mixture is kept at 105° C. for 2 hours under nitrogen.

At the end of this period, analysis indicates the presence of 2.2 g of hydroquinone monomethyl ether (conversion 45%, selectivity 88%).

At this point, the autoclave is cooled to 60° and pressurised to 2 kg/cm$^2$ with O$_2$.

When the pressure falls by 1 kg/cm$^2$ (about 15 minutes) the residual gas is replaced by a blanket of nitrogen, and the autoclave is again heated to 105° C. for 2 hours. At the end of this period, analysis indicates the presence of 4.1 g of hydroquinone monomethyl ether (conversion 90%, selectivity 81%).

EXAMPLE 14

5.0 g of hydroquinone, 40 cm³ of methanol and 0.25 g of CuCl₂ are fed into a flask fitted with a reflux condenser, stirrer and air feed bubbler.

The system is kept under reflux for 8 hours, during which a strong air stream is bubbled into the liquid.

On termination, analysis indicates the formation of 3.9 g of hydroquinone monomethyl ether (conversion 75%, selectivity 90%).

EXAMPLE 15

A catalyst is prepared by percolating a methanol solution of CuCl₂ through a bed of sulphonated styrene resin (Amberlyst 15) until there is no further presence of acidity in the eluted liquid.

2.25 g of the resin subjected in this manner to ion exchange and then dried are fed into the autoclave with 5.0 g of hydroquinone and 40 cm³ of methanol. It is pressurised to 3 kg/cm² with O₂ and kept at 105° for 3 hours. 3.7 g of hydroquinone monomethyl ether are obtained (conversion 80%, selectivity 82%).

The catalyst is recovered by filtration, washed with methanol and dried under vacuum. A test identical to that heretofore described is carried out using this recovered catalyst, to obtain 3.6 g of hydroquinone monomethyl ether. In a third catalyst recycling test under the same conditions, a further 3.6 g of hydroquinone monomethyl ether are obtained.

EXAMPLE 16

A catalyst is prepared by treating 10 g of sulphonated styrene resin (Amberlyst 15) with 50 cm³ of a 0.20 molar methanol solution of CuCl₂.

The resin, when filtered and dried, contains $0.7 \times 10^{-3}$ equivalents of copper per gram of resin.

2.0 g of the catalyst prepared in this manner are fed into the autoclave with 5.0 g of hydroquinone and 40 cm³ of methanol.

The autoclave is pressurised to 5 kg/cm² with O₂ and kept at 105° C. for 4 hours. 3.4 g of hydroquinone monomethyl ether are obtained (conversion 75%, selectivity 81%).

The catalyst is recovered by filtration, washed with methanol and dried, and used in a test identical to the preceding. 3.9 g of hydroquinone monomethyl ether are obtained (conversion 85%, selectivity 81%).

EXAMPLE 16A 2.0 g of the catalyst prepared as in the preceding test are fed into the autoclave with 5.0 g of hydroquinone and 40 cm³ of methanol. The autoclave is kept at 105° C. for 4 hours under nitrogen. 0.25 g of hydroquinone monomethyl ether are obtained.

EXAMPLE 16B 5.0 g of hydroquinone, 40 cm³ of methanol and 1.0 g of sulphonated styrene resin (Amberlyst 15) are fed into the autoclave. The autoclave is pressurised to 5 kg/cm² with O₂ and kept at 105° for 4 hours. 1.04 g of hydroquinone monomethyl ether are obtained (18%).

EXAMPLE 17

The test described in the preceding example is repeated with the addition of 0.200 g of CuCl. 4.7 g of hydroquinone monomethyl ether are obtained (conversion 95%, selectivity 88%).

EXAMPLE 18

A catalyst is prepared by treating 10 g of sulphonated styrene resin (Amberlyst 15) with 50 cm³ of a 0.13 molar solution of anhydrous FeCl₃ in methanol.

After being filtered, washed with methanol and dried, the resin contains 1.0 milliequivalent of iron per gram of resin. 2.0 g of the catalyst prepared in this manner are fed into the autoclave together with 5.0 g of hydroquinone and 40 cm³ of methanol. The autoclave is pressurised to 5 kg/cm² with O₂ and kept at 105° for 4.5 hours. 4.1 g of hydroquinone monomethyl ether are obtained (conversion 80%, selectivity 91%).

EXAMPLE 19

The catalyst is recovered from the preceding test by filtration, washed with methanol and dried under vacuum, and is again fed into the autoclave together with 5.0 g of tert-butyl-hydroquinone and 40 cm³ of methanol. It is pressurised to 5 kg/cm² with O₂ and kept at 105° for 4 hours. 3.4 g of tert-butyl-hydroquinone monomethyl ether (BHA) are obtained (conversion 100%, selectivity 63%).

The two BHA isomers (3-tert-butyl-4-hydroxyanisole and 2-tert-butyl-4-hydroxyanisole) are formed in a weight ratio of 96:4.

We claim:

1. A process for preparing monoalkylethers of hydroquinone and of substituted hydroquinones of general formula

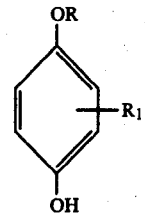

in which R is an alkyl group and R₁ is hydrogen or an alkyl group, characterised in that a hydroquinone compound of general formula

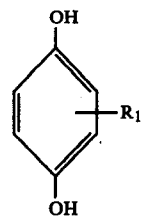

is reacted with an alcohol of formula R—OH in the presence of a transition metal salt selected from copper and iron salts, at a temperature of from 25° C. to 150° C.

2. A process as claimed in claim 1 wherein the reaction is carried out in the presence of air or oxygen.

3. A process as claimed in claim 1 wherein the reaction is carried out in the absence of oxygen or air.

4. A process as claimed in claim 3 wherein said transition metal salts are selected from chlorides and sulphates of bivalent copper and trivalent iron optionally supported on an ion-exchange resin material.

5. A process as claimed in claim 3 wherein the transition metal salt is used in a weight ratio of between 1:50 and 1:1 with respect to the hydroquinone substrate.

6. A process as claimed in claim 2 wherein the air or oxygen is supplied to the reaction system at atmospheric or above-atmospheric pressure, or by bubbling into the reaction system.

7. A process as claimed in claim 2 wherein said transition metal salts are selected from chlorides and sulphates of copper in the valency states 1 and 2 and of iron in the valency states 2 and 3, optionally supported on an ion exchange resin material.

8. A process as claimed in claim 2 wherein the transition metal salt is used in a weight ratio of between 1:1000 and 1:2 with respect to the hydroquinone substrate.

9. A process as claimed in claim 7 wherein said ion exchange resin material is a sulfonated styrene resin.

10. A process as claimed in claim 4 wherein said ion exchange resin material is a sulfonated styrene resin.

* * * * *